United States Patent [19]
Morsiani et al.

[11] Patent Number: 5,968,356
[45] Date of Patent: Oct. 19, 1999

[54] SYSTEM FOR HEPATOCYTE CELL ISOLATION AND COLLECTION

[75] Inventors: Eugenio Morsiani, Ferraro, Italy; Jacek Rozga, Westlake Village; Achilles A. Demetriou, Bel Air, both of Calif.

[73] Assignee: PacFab, Inc., Moorpark, Calif.

[21] Appl. No.: 09/240,731

[22] Filed: Jan. 29, 1999

Related U.S. Application Data

[63] Continuation of application No. 08/484,717, Jun. 8, 1995, Pat. No. 5,888,409.

[51] Int. Cl.[6] .................................................. B01D 37/00
[52] U.S. Cl. .................. 210/335; 210/314; 210/323.1; 210/388; 210/435; 210/446; 210/489; 210/499; 422/101; 422/102; 604/406
[58] Field of Search .................................. 210/323, 314, 210/321.75, 388, 433.1, 435, 446, 450, 488, 489, 499, 650, 767, 800; 422/101, 102; 604/406; 635/267, 268

[56] References Cited

U.S. PATENT DOCUMENTS

| | | |
|---|---|---|
| 2,895,615 | 7/1959 | Oathout . |
| 2,999,560 | 12/1961 | Seefluth . |
| 4,395,493 | 7/1983 | Zahniser et al. . |
| 4,685,472 | 8/1987 | Muto . |
| 4,954,251 | 9/1990 | Barnes et al. . |
| 5,039,386 | 8/1991 | Margolis . |
| 5,085,773 | 2/1992 | Danowski . |
| 5,185,086 | 2/1993 | Kaali et al. . |
| 5,280,377 | 1/1994 | Galvan . |
| 5,301,685 | 4/1994 | Guirguis . |
| 5,328,614 | 7/1994 | Matsumura . |
| 5,368,729 | 11/1994 | Stefkuvich et al. . |
| 5,372,945 | 12/1994 | Alchas et al. . |
| 5,409,833 | 4/1995 | Hu et al. . |

FOREIGN PATENT DOCUMENTS

| | | |
|---|---|---|
| 0306206A1 | 8/1988 | European Pat. Off. . |
| 0471570A1 | 8/1991 | European Pat. Off. . |
| 0483506A1 | 9/1991 | European Pat. Off. . |
| 2019919A | 4/1979 | United Kingdom . |
| WO 94/03103 | 7/1993 | WIPO . |

OTHER PUBLICATIONS

"Large–Scale Production and Cultivation of Hepatocytes on Biosilon Microcarriers," Alexander, S. et al,, Artif Organs, vol. 14, No. 6 1990, pp. 421–428.

"High–Yield Preparation of Porcine Hepatocytes for Long Survival after Transplantation in the Spleen," Nordlinger, B. et al., European Surgical Research, 17:377–382 (1985).

"Use of a Low–Speed, Iso–Density Percoll Centrifugation Method to Increase The Viability of Isolated Rat Hepatocyte Preparations," Kreamer, B., et al., In Vitro Cellular & Developmental, vol. 22, No. 4, 1986.

*Primary Examiner*—David A. Reifsnyder
*Attorney, Agent, or Firm*—Pretty, Schroeder & Poplawski, P.C.

[57] ABSTRACT

The invention resides in apparatus and methods for isolating and collecting cells from donor tissue for later use in medical procedures. The apparatus includes a sealed enclosure, at least one screening material inside the enclosure, an inlet port configured to conduct a fluid through the screening material, and an outlet port for receiving the fluid from the screening material and conducting the fluid out of the enclosure. A material to be screened is placed inside or conducted into the enclosure. Screened material is entrained in the fluid. The fluid carries bits of the material through the screening material and out of the enclosure for later separation from the fluid. Preferred embodiments include a series of screening materials of decreasing pore size, usually in the range from ten to one thousand micrometers in diameter. A particularly preferred embodiment includes three distinct screening materials having pore sizes of 400 micrometers, 280 micrometers, and 100 micrometers, listed in the order that the fluid passes through the screening materials. The invention is used in the collection and isolation of porcine hepatocytes for later use in medical procedures. The sealed enclosure is constructed of a series of individual segments held together by conveniently removable fasteners—bolts and wing nuts. A mechanical shaker agitates the enclosure as the fluid flows over and through the material being screened.

18 Claims, 2 Drawing Sheets

SYSTEM FOR HEPATOCYTE CELL ISOLATION AND COLLECTION

The present application is a continuation of U.S. patent application Ser. No. 08/484,717, filed Jun. 8, 1995, now U.S. Pat. No. 5,888,409 and the entire disclosure of such prior application is hereby incorporated herein by reference.

BACKGROUND OF THE INVENTION

The invention relates generally to apparatus and methods for isolating and collecting living cells for later use in medical procedures. More particularly, the invention relates to apparatus and related methods in which living cells from a human or animal donor are isolated and collected inside a sealed enclosure. After collection, the isolated cells can be removed from the enclosure for use in medical procedures.

The development of new medical procedures has lead to a need for improved apparatus and methods for isolating and collecting living cells from human and animal donors. In certain types of cell therapy, living cells from a donor are injected into a patient. Those cells lodge inside the patient's body and function to provide a therapeutic benefit to the patient. As an illustrative example, cell therapy is coming into increasing use in the treatment of diseases and injuries to the human liver.

In some cell therapy methods, healthy liver tissue is taken from an animal donor, which is often a pig. The liver tissue is chemically treated to break down, or "digest," the structure of the liver. The digested liver tissue is then filtered to isolate and collect hepatocytes, i.e., living, functional liver cells.

The collected cells are then injected or implanted into a diseased or injured liver or elsewhere inside a human patient. The donated cells lodge inside the patient, where they act to assist and augment the functioning of the recipient's own diseased or injured liver. The functioning of the patient's liver is significantly enhanced by the presence of these donor cells, and the patient enjoys a distinct therapeutic benefit.

The practicability of cell therapy treatment of the liver and related cell therapy techniques is obviously dependent upon the availability of sufficient quantities of healthy liver cells from a donor. Currently, digested liver tissue is most often processed by washing and filtering the digested tissue manually through one or more screens or meshes having openings or pores of appropriate size.

Known techniques for collecting and isolating living cells are less than ideal. Processing the cells by manual washing and filtration is time consuming and labor intensive. The cells can be damaged, killed or otherwise rendered incapable of performing their desired functions due to rough handling. Moreover, known methods are typically performed in "open" procedures in which the tissue and cells are not contained inside any closed container. This may compromise the sterility of the cells collected and isolated using the known methods.

A definite need exists, therefore, for apparatus and methods for isolating and collecting cells in which cell harvesting can be made quicker and less labor intensive, damage to the cells substantially reduced, and sterility of the collected cells made more secure.

SUMMARY OF THE INVENTION

The present invention, which addresses this need, resides in novel apparatus and methods for isolating and collecting cells from donor tissue for later use in medical procedures. Apparatus embodying the invention includes a sealed enclosure, at least one screening material inside the enclosure, an inlet port configured to conduct a fluid through the screening material, and an outlet port for receiving the fluid from the screening material and conducting the fluid out of the enclosure. In use, a material to be screened is placed inside or conducted into the enclosure. Screened material is entrained in the fluid which carries it through the screening material and out of the enclosure for later separation from the fluid.

Preferred embodiments include a series of screening materials of decreasing pore size, usually in the range from ten to one thousand micrometers in diameter. A particularly preferred embodiment includes three distinct screening materials having pore sizes of 400 micrometers, 280 micrometers, and 100 micrometers, listed in the order that the fluid passes through the screening materials.

This embodiment has been found useful in the collection and isolation of porcine hepatocytes for later use in medical procedures.

In the particularly preferred embodiment of the invention, the sealed enclosure is constructed of a series of individual segments held together by conveniently removable fasteners—bolts and wing nuts. This construction allows for quick and convenient assembly and disassembly of the apparatus, e.g., for cleaning.

It is advantageous to agitate the enclosure using a mechanical shaker as the fluid is flowing over and through the material to be screened. Agitation of the enclosure is a step of a preferred method according to the invention.

The invention provides improved apparatus and methods for isolating and collecting biological cells. The invention makes this process quicker and less labor intensive, with less chance of contamination, than apparatus and methods that have previously been used for this purpose. Moreover, cells isolated using the invention have been found to suffer less damage and retain greater functioning than cells isolated according to previously known apparatus and methods. Other features and advantages of the present invention will become apparent from the following detailed description of the preferred embodiment, taken in conjunction with the accompanying drawings, which illustrate by way of example the principles of the invention.

DESCRIPTION OF THE PREFERRED EMBODIMENTS

Figure 1:
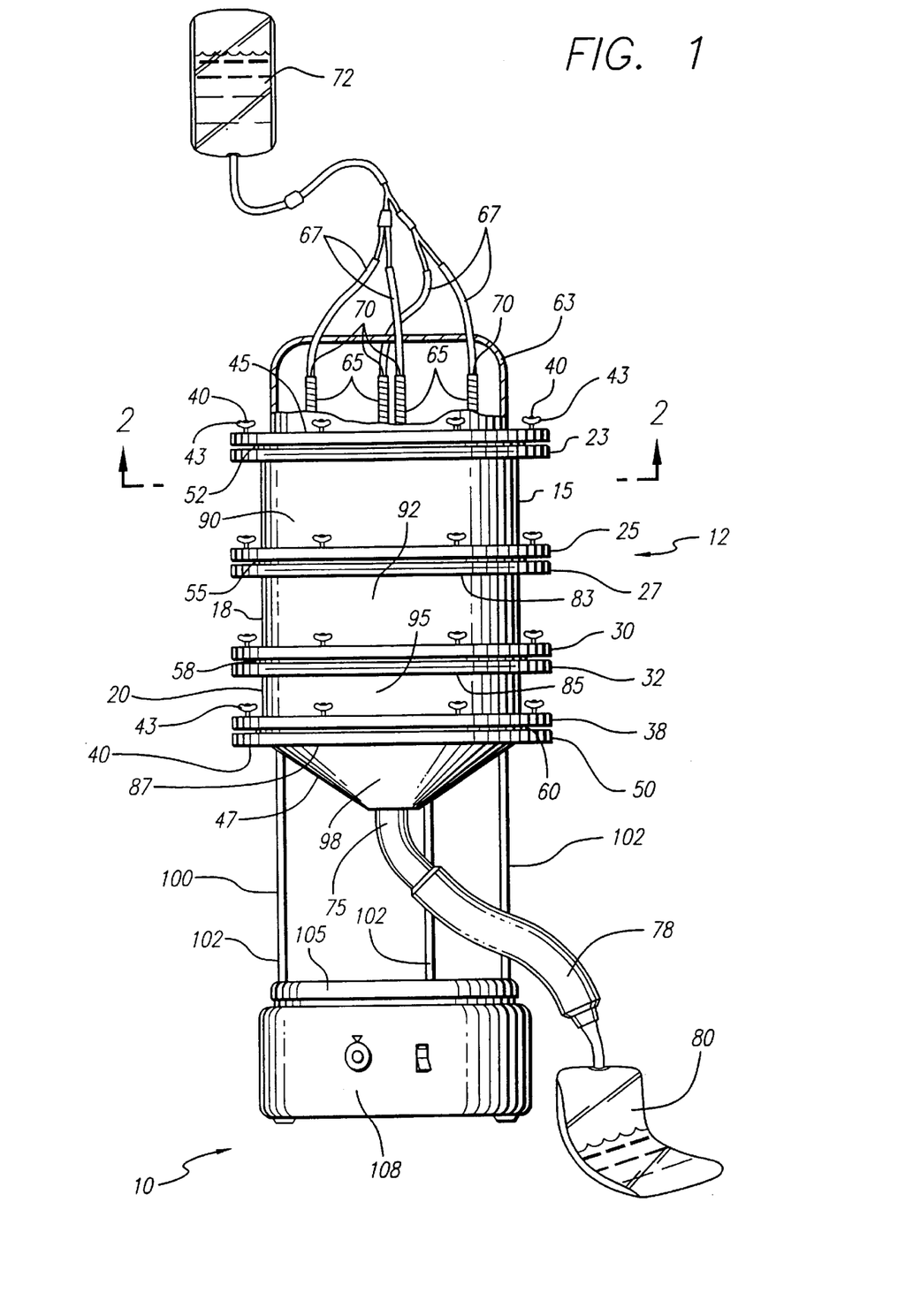
FIG. 1 is a side sectional view of apparatus adapted for the isolation and collection of cells from donor tissue.

FIG. 1 depicts a system 10 adapted for use in the isolation and collection of living cells for later use in medical procedures. As depicted therein, the system includes a cylindrical enclosure 12 constructed of a plurality of stacked annular segments 15, 18, and 20. These segments are fastened together to form the drum-like cylindrical enclosure.

Each annular segment includes an upper and a lower flange. Annular segment 15 includes an upper flange 23 and a lower flange 25, segment 18 includes an upper flange 27 and a lower flange 30, and segment 20 includes an upper flange 32 and a lower flange 38. As depicted in FIG. 1, the upper and lower flanges of adjacent segments are secured to one another by means of fasteners. In the preferred embodiment these fasteners are bolts 40 and wing nuts 43. This arrangement allows for convenient assembly and disassembly of the system when access to the interior of the enclosure 12 is required during use or for cleaning.

The cylindrical enclosure 12 is closed at its top and bottom ends, respectively, by an end plate 45 and a collection funnel 47. The end plate 45 is fastened to the upper flange 23 of annular segment 15 by bolts 40 and wing nuts 43. The collection funnel 47 includes a funnel flange 50, which is secured to the lower flange 38 of annular segment 20. Flexible O-rings 52, 55, 58, and 60 act as gaskets providing secure and reliable fluid-tight seals between adjacent parts of the enclosure. The end plate 45 has a handle 63 affixed to it so that the end plate can be conveniently removed from and installed against the upper flange 23 of the uppermost annular segment 15.

Although the end plate 45 depicted in FIG. 1 is in the form of a flat circular plate, other configurations may prove equally useful. For example, the "end plate" could be in the form of a conical or hemispherical enclosure. Any part configured to seal an end of the enclosure 12 may be considered an "end plate" as that term is used herein.

The end plate 45 further includes a plurality of inlet ports 65. Segments of inlet tubing 67 are connected to each of the inlet ports. Flexible coil springs 70 hold the inlet tubing straight in the region of the inlet ports so that an appropriate fluid can be conducted without restriction into the enclosure 12 from a supply bag 72 connected to the inlet tubing. At the bottom of the enclosure, an outlet port 75 at the tip of the collection funnel 47 allows fluid to drain out of the enclosure through a collection hose 78 and into a collection bag 80. The flow of fluid from the supply bag, through the enclosure, and into the collection bag will be described in more detail below.

The constituent parts described above form a cylindrical enclosure 12 having an internal volume of approximately five liters. This internal volume is divided by mesh screening materials 83, 85, and 87 into three cylindrical chambers 90, 92, and 95, and a generally conical drain region 98 enclosed by the collection funnel 47. The individual screening materials are sandwiched between and held in place by the flanges 25, 27, 30, 32, 38, and 50 of the annular segments 15, 18, and 20, and the collection funnel 47. Although the preferred embodiment described herein includes three screening materials dividing adjacent chambers, it should be appreciated that more or fewer screening materials could be used, and the number of chambers varied thereby without departing in any way from the principles of the present invention.

Figure 2:
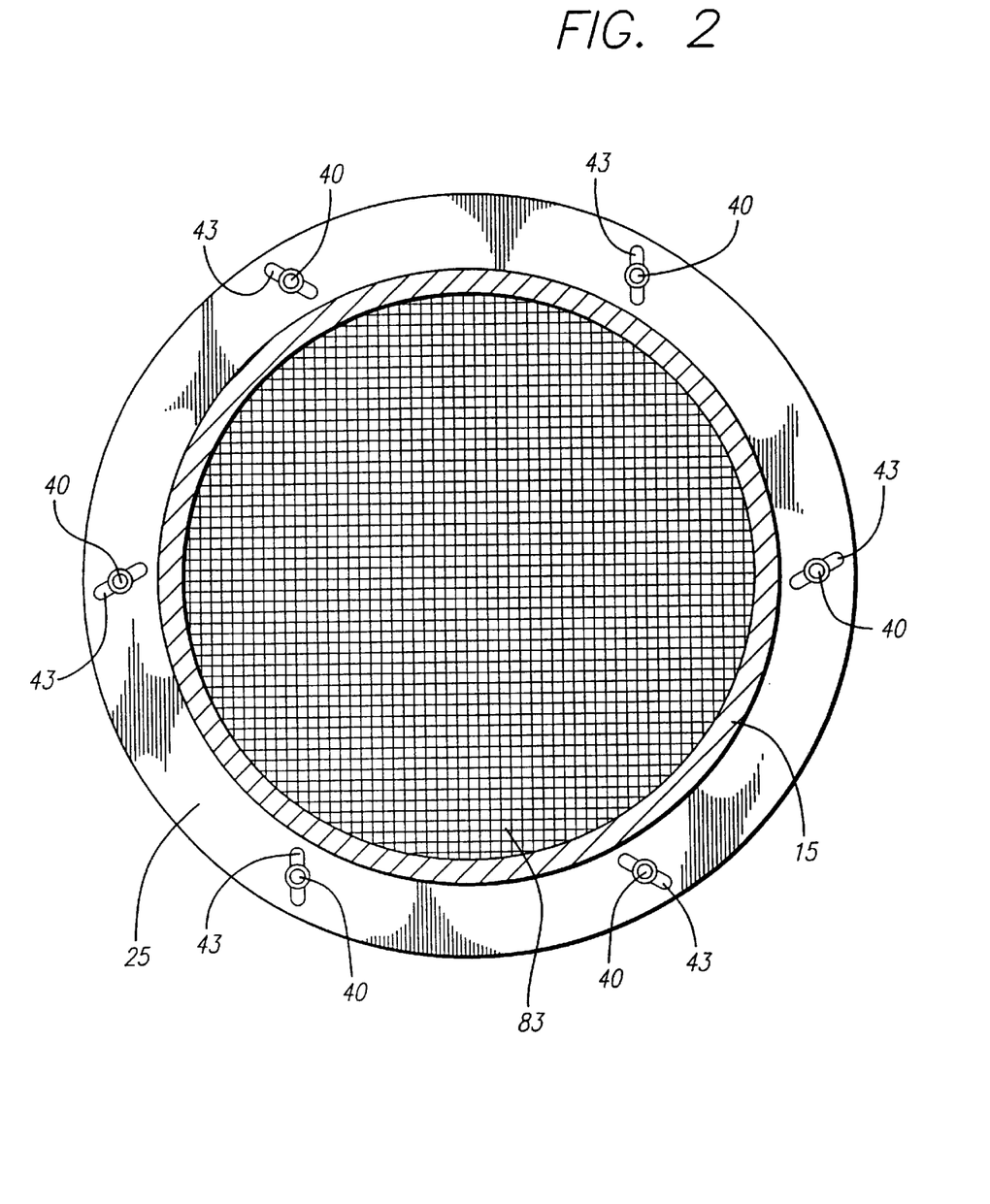
FIG. 2 is a plan view taken along section lines 2—2 of FIG. 1.

FIG. 2 is a plan view taken along section lines 2—2 of FIG. 1. FIG. 2 shows a section of the uppermost annular segment 15, that segment's lower flange 25, and the bolts 40 and wing nuts 43 that secure the lower flange of segment 15 to the upper flange (27, see FIG. 1) of segment 18.

FIG. 2 also shows the uppermost mesh screening material 83. As depicted therein, the screening material is a mesh material including a large number of openings or pores. The pores depicted in FIG. 2 are not to scale. The actual pores are much smaller than FIG. 2 would indicate. The screening material used in the actual apparatus is described in more detail below.

The materials chosen for the system 10 should provide the desired qualities of durability, ease of assembly, and convenience of cleaning and sterilization.

The annular segments 15, 18, and 20, the end plate 45, and the collection funnel 47 may all be formed of stainless steel or a similar suitable material. The material chosen for these parts is preferably durable enough to withstand repeated assembly, use, and disassembly, and should also be one that can be conveniently cleaned and sterilized. Additionally, the interior surfaces of the enclosure 12 is advantageously smooth so that cells and fluids flow smoothly through the enclosure. Finally, the material chosen is preferably easy to machine or otherwise shape so that the various parts can be formed conveniently and economically.

The O-rings 52, 55, 58, and 60 should be formed of a synthetic rubber or a similar flexible, durable material that provides a secure and reliable fluid-tight seal. The screening materials 83, 85, and 87 can be made of porous nylon sheets of appropriate size. Significantly, each of the individual screening materials has pores of preselected size. Generally, the pore size of the screening material will decrease from the upper to the lower part of the apparatus. The pore sizes of the different screening materials will generally fall within the range from ten to one thousand micrometers. In a particular embodiment of the invention, first screening material 83 includes pores approximately 400 micrometers in diameter, second screening material 85 has pores of about 280 micrometers, with third screening material 87 having pores of about 100 micrometers. The screening materials described herein are available from Tetko Inc. of Lancaster, N.Y.

Screening materials having pores of the specified sizes have been found useful in the present invention.

Typical hepatocytes are about 20 micrometers in diameter.

The intent of the inventors in choosing the specified screening materials is to isolate mainly single hepatocytes with some doublets or triplets but few clusters comprised of more than three cells. The pore sizes of the selected screening materials could be varied somewhat without unduly impairing the performance of the invention.

The inlet tubing 67 and collection hose 78 can be made of an appropriate medical grade plastic or synthetic rubber as is conventional in medical applications. The supply bag 72 and collection bag 80 will typically be of the type commonly used in medical applications to hold blood, saline, or other fluids.

The assembled enclosure 12 is mounted on a pedestal 100 having legs 102 affixed to a base 105. The base of this pedestal is in turn positioned on a mechanical shaker 108. The shaker can be, for example, a Red Rotors™ orbital shaker, available from Hoefer Scientific Instrument, Inc. of San Francisco, Calif.

Use of the system 10 to isolate and collect biological cells will be described below. In a preferred method, the end plate 45 is lifted off the top of the enclosure 12 to allow access to the interior of the enclosure. Chemically digested liver material from a suitable donor is placed inside the enclosure on top of the uppermost screening material 83. This liver material is in part a mass of cells including the hepatocytes that are to be collected, and in part extraneous materials from which those cells are to be isolated.

The mechanical shaker is operated to gently oscillate the enclosure at 60 oscillations per minute.

While the enclosure 12 is being shaken gently by the shaker 108, fluid from the supply bag 72 is conducted through the inlet tubing 67 into the upper portion of the enclosure and over the digested liver material. Ice-cold Dulbecco's Modified Eagle's Medium (DMEM; Sigma Chemicals, Saint Louis, Miss.) fortified with 10% bovine calf serum (BCS; Hyclone Laboratories, Inc., Logan, Utah) has been found to be a suitable fluid for use with digested porcine liver material.

As depicted in FIG. 1, the inlet ports 65 are configured to conduct fluid over the digested liver material and through the screening materials 83, 85, and 87. The fluid percolates over and through the liver material. Viable hepatocytes are entrained within the fluid and screened through each of the screening materials in sequence. From the screening materials, the fluid and entrained cells flow through the outlet port 75 out of the enclosure 12 and into the collection bag 80.

The supply bag 72 and collection bag 80 seal the enclosure 12 and prevent communication of materials or pathogens from the outside environment. This sealed enclosure ensures sterility of the interior and contents of the system 10. Sterility of the collected cells is thereby made more secure than in conventional methods in which the cells are collected in open containers exposed to the environment.

When a satisfactory amount of cells and fluid has collected inside the collection bag 80, which may take several minutes, the collection bag holding the screened cell/fluid suspension is removed from the enclosure 12 and subjected to automated centrifugation and washing in a COBE 2991 blood cell processor, available from Blood Component Technology of Lakewood, Colo.

What is claimed is:

1. A system for collecting cells, the system comprising:
    a fluid having single hepatocyte cells and clusters of multiple hepatocyte cells;
    a sealed enclosure:
        first and second screening materials situated inside the enclosure, each screening material defining pores of a predetermined size with pores in the first material being of a different size than pores in the second material, the screening materials being configured to isolate for collection more single hepatocyte cells than clusters;
        an inlet port configured to conduct a fluid through the first and second screening materials; and
        an outlet port configured to receive the fluid from the first and second screening materials and to conduct the fluid out of the enclosure, wherein the fluid received from the screening materials contains single hepatocyte cells and clusters;
        whereby the fluid conducted out of the enclosure and collected contains more single hepatocyte cells than clusters.

2. The system of claim 1, wherein the screening materials includes pores having a diameter of between approximately ten and one thousand micrometers.

3. The system of claim 1, wherein the sealed enclosure comprises a plurality of segments joined to one another.

4. The system of claim 3, wherein each of the screening materials is disposed between adjacent segments of the sealed enclosure.

5. The system of claim 3, wherein the segments include flanges adapted for use with fasteners to hold the segments to one another.

6. The system of claim 1, wherein the pores of the first screening material are configured to filter out matter exceeding about 280 micrometers; and
    the pores of the second screening material are configured to filter out matter exceeding about 100 micrometers.

7. The system of claim 6, further including a third screening material that defines pores of different predetermined size relative to the respective sizes of pores defined in the first and second materials.

8. The system of claim 7, wherein the third screening material is configured to filter out matter exceeding about 400 micrometers.

9. The system according to claim 1, further including a shaker for oscillating the enclosure.

10. A system for collecting cells, the system comprising:
    a fluid having single hepatocyte cells and clusters of multiple hepatocyte cells;
    a sealed enclosure comprising a plurality of segments disposed against one another;
    an end plate joined to an end of one of the segments:
    an inlet port in fluid communication with the interior of the sealed enclosure;
    a collection funnel joined to an end of one of the segments;
    an outlet port in fluid communication with the interior of the sealed enclosure; and
    a plurality of screening materials disposed inside the sealed enclosure between the inlet port and the outlet port, the screening materials each defining pores of different predetermined size, the screening materials being configured to isolate for collection more single hepatocyte cells than clusters;
    whereby, after the fluid passes through the screening materials, the fluid contains more single hepatocyte cells than clusters.

11. The system of claim 10, wherein each of the screening materials is disposed between adjacent segments of the sealed enclosure.

12. The system according to claim 10, further including a shaker for oscillating the enclosure.

13. A system for collecting hepatocyte cells, the apparatus comprising:
    fluid entraining hepatocyte cells;
    an enclosure adapted to retain the fluid, the enclosure heaving inlet and outlet ports for respectively transmitting the fluid to and from the enclosure; and
    a first screening material disposed within the enclosure, the first screening material having a plurality of first pores, each of which is configured to filter out matter exceeding 100 micrometers;
    whereby hepatocyte cells not exceeding about 100 micrometers exits through the outlet port.

14. The system according to claim 13, wherein the hepatocyte cells are initially contained within a biological material situated within the enclosure.

15. The system according to claim 13, further including a second screening material disposed within the enclosure, the second material having a plurality of second pores that are different in size than the first pores.

16. The system according to claim 13, further including a shaker for oscillating the enclosure.

17. A system for collecting cells, the system comprising:
    an end plate;
    a first segment joined to the end plate;

a second segment joined to the first segment;

a first screening material disposed between the first and second segments;

a third segment;

a second screening material disposed between the second and third segments;

a collection funnel;

a third screening material disposed between the third segment and the collection funnel;

wherein the segments define an enclosure that includes an inlet port and an outlet port, each in fluid communication with the interior of the enclosure; and a fluid having single hepatocyte cells and clusters of single hepatocyte cells;

wherein the screening materials are disposed between the inlet port and the outlet port and are configured for cell isolation such that substantially more single hepatocyte cells are collected than clusters;

whereby the fluid exiting the outlet port contains more single hepatocyte cells than clusters.

18. The system according to claim 17, further including a shaker for oscillating the enclosure.

* * * * *

UNITED STATES PATENT AND TRADEMARK OFFICE
CERTIFICATE OF CORRECTION

PATENT NO. : 5,968,356
DATED : October 19, 1999
INVENTOR(S) : Morsiani, Eugenio, et. al.

It is certified that error appears in the above-identified patent and that said Letters Patent is hereby corrected as shown below:

Title page, item [63], delete "Jun. 8, 1995" and insert --Jun. 7, 1995--

Claim 2, delete "includes" and insert --include--.
Claim 13, delete "heaving" and insert --having--.
Col. 1, in the specification after the title delete "Jun.8, 1995" and insert --Jun. 7, 1995--

Signed and Sealed this

First Day of May, 2001

Attest:

NICHOLAS P. GODICI

Attesting Officer

Acting Director of the United States Patent and Trademark Office

UNITED STATES PATENT AND TRADEMARK OFFICE
CERTIFICATE OF CORRECTION

PATENT NO.   : 5,968,356
DATED        : October 19, 1999
INVENTOR(S)  : Jan Rose Heeg, Rolfe Frank Kruckas, Ashok Murthy, Stephen Todd Olson, Jeanne Marie Saldanah-Singh, Rita Sharma, Ajay Kanubhai Suthar, Richard Barber Watkins, Joe William Woods It is certified that error appears in the above-identified patent and that said Letters Patent is hereby corrected as shown below:

Claim 3,
Line 1, Change "substrate" to read -- sheet --.

Claim 5,
Line 1, Change "substrate" to read -- sheet --.

Claim 6,
Line 1, Change "substrate" to read -- sheet --.

Claim 7,
Line 1, Change "substrate" to read -- sheet --.

Claim 8,
Line 1, Change "substrate" to read -- sheet --.

Signed and Sealed this

Thirty-first Day of July, 2001

*Attest:*

Nicholas P. Godici

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO. : 5,968,356
DATED : October 19, 1999
INVENTOR(S) : Eugenio Morsiani et al.

It is certified that error appears in the above-identified patent and that said Letters Patent is hereby corrected as shown below:

Title page,
Item [73], Assignee, delete "PacFab., Inc., Moorpark, Calif." and insert therefor
-- Cedars-Sinai Medical Center, Los Angeles, Calif. --.

Signed and Sealed this

Fifteenth Day of January, 2002

Attest:

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.    : 5,968,356
DATED         : October 19, 1999
INVENTOR(S)   : Eugenio Morsiani et al.

It is certified that error appears in the above-identified patent and that said Letters Patent is hereby corrected as shown below:

This certificate supersedes Certificate of Correction issued July 31, 2001, the number was erroneously mentioned and should be deleted since no certificate of correction was granted.

Signed and Sealed this

Third Day of September, 2002

Attest:

Attesting Officer

JAMES E. ROGAN
Director of the United States Patent and Trademark Office